United States Patent [19]

Sestanj et al.

[11] Patent Number: 4,672,059
[45] Date of Patent: Jun. 9, 1987

[54] N-[[5-(TRIFLUOROMETHYL)-6-METHOXY-1-NAPHTHALENYL]-THIOXOMETHYL AND CARBONYL]-N-METHYLGLYCINAMIDES

[75] Inventors: Kazimir Sestanj, Monmouth Junction; Eckhardt S. Ferdinandi, Princeton, both of N.J.

[73] Assignee: American Home Products Corporation, New York, N.Y.

[21] Appl. No.: 799,036

[22] Filed: Nov. 18, 1985

Related U.S. Application Data

[63] Continuation-in-part of Ser. No. 743,336, Jun. 10, 1985.

[51] Int. Cl.$^4$ ............................................. A61K 31/70
[52] U.S. Cl. ................................................. 514/62; 558/8; 514/563; 514/588; 514/599; 514/866; 536/55.2; 536/53; 536/55; 564/44; 564/74; 564/157

[58] Field of Search ................... 536/55.2; 564/44, 74, 564/157; 514/62, 563, 588, 599; 260/453.9

[56] References Cited

U.S. PATENT DOCUMENTS

Re. 30,563  3/1981  Abdulla et al. .................. 564/44
2,135,064  11/1938  Whitmore et al. ............... 564/44
3,081,302  3/1963  Shapiro et al. .................. 564/157
4,282,169  8/1981  Rothgery et al. ................ 564/74
4,318,924  3/1982  Fest et al. ....................... 564/44
4,439,617  3/1984  Sestanj ............................ 560/39

Primary Examiner—Johnnie R. Brown

[57] ABSTRACT

Disclosed herein are tolrestat and oxotolrestat amides and methods of preparation. The amides are new aldose reductase inhibitors useful for the treatment or prevention of diabetic complications.

7 Claims, No Drawings

N-[[5-(TRIFLUOROMETHYL)-6-METHOXY-1-NAPHTHALENYL]-THIOXOMETHYL AND CARBONYL]-N-METHYLGLYCINAMIDES

This is a continuation-in-part application of copending U.S. Ser. No. 743,336, filed June 10, 1985.

BACKGROUND OF THE INVENTION

This invention relates to N-[[5-(trifluoromethyl)-6-methoxy-1-naphthalenyl]-thioxomethyl and carbonyl]-N-methylglycinamides, to processes for their preparation, to methods for using the derivatives, and to pharmaceutical preparations thereof. The derivatives have pharmaceutical properties which render them beneficial for the treatment of diabetes mellitus and associated conditions.

For many years diabetes mellitus has been treated with two established types of drugs, namely insulin and oral hypoglycemic agents. These drugs have benefited hundreds of thousands of diabetics by improving their well-being and prolonging their lives. However, the resulting longevity of diabetic patients has led to complications such as neuropathy, nephropathy, retinopathy, cataracts and atherosclerosis. These complications have been linked to the undesirable accumulation of sorbitol in diabetic tissue, which in turn resulted from the high levels of glucose characteristic of the diabetic patient.

In mammals, including humans, the key enzyme involved in the conversion of hexoses to polyols (e.g. the sorbitol pathway) is aldose reductase. J. H. Knoshita and collaborators, see J. H. Kinoshita et al., Biochem. Biophys, Acta, 158, 472 (1968) and references cited therein, have demonstrated that aldose reductase plays a central role in the etiology of galactosemic cataracts by effecting the conversion of galactose to dulcitol (galactitol) and that an agent capable of inhibiting aldose reductase can prevent the detrimental accumulation of dulcitol in the lens. Furthermore, a relationship between elevated levels of glucose and an undesireable accumulation of sorbitol has been demonstrated in the lens, peripheral nervous cord and kidney of diabetic animals, see A. Pirie and R. van Heyningen, Exp. Eye Res., 3, 124 (1964); L. T. Chylack and J. H. Kinoshita, Invest. Ophthal., 8, 401 (1969) and J. D. Ward and R. W. R. Baker, Diabetol., 6, 531 (1970).

1,3-Dioxo-1H-benz[de]isoquinoline-2(3H)-acetic acid has been reported to be an effective inhibitor of aldose reductase, see D. Dvornik et al., Science, 182, 1146 (1973), and to be useful for the treatment of diabetic complications such as diabetic cataracts, neuropathy, nephropathy and retinopathy, see K. Sestanj, N. Simard-Duquesne and D. Dvornik, U.S. Pat. No. 3,821,383, June 28, 1974. Other compounds having a similar utility are the thioxo-1H-benz[de]isoquinoline-3(3H)-acetic acid derivatives of K. Sestanj, U.S. Pat. No. 4,254,108, Mar. 3, 1981 and 1H-benz[de]isoquinoline-2(3H)-acetic acid derivatives of K. Sestanj, U.S. Pat. No. 4,254,109, Mar. 3, 1981. Still other compounds having a similar utility are 2-thioxobenz[c,d]indole-1(2H)-acetic acid derivatives of K. Sestanj, U.S. Pat. No. 4,369,188, Jan. 18, 1983; N-naphthoylglycine derivatives of K. Sestanj et al., U.S. Pat. No. 4,439,617, Mar. 27, 1984; N-(naphthalenylthioxomethyl)amino acid derivatives of K. Sestanj et al., U.S. Pat. No. 4,391,816, July 5, 1983; N-[(2-naphthalenyl)thioxomethyl]glycine derivatives of K. Sestanj, U.S. Pat. No. 4,447,452, May 8, 1984; and N-[[6-(lower alkoxy)-5-(trifluoromethylthio)-1-naphthalenyl]thioxomethyl]-N-(lower alkyl)-glycines of F. Bellini et al., U.S. Pat. No. 4,391,825, July 5, 1983. (S)-6-Fluoro-2,3-dihydrospiro(4H-1-benzopyran-4,4'-imidazolidine)-2',5'-dione (sorbinil) is still another compound that has received attention because of its aldose reductase inhibiting properties (see M. J. Peterson et al., Metabolism 28 (Suppl. 1), 456 (1979). Accordingly, these compounds represent an important new approach for the treatment of diabetes mellitus.

The present application discloses novel N-[[5-(trifluoromethyl)-6-methoxy-1-naphthalenyl]-thioxomethyl and carbonyl]-N-methylglycinamides represented below by formula I, which are effective inhibitors of aldose reductase. These are structurally different from the above noted aldose reductase inhibitors.

The closest of the previously reported compounds is seen in U.S. Pat. No. 4,439,617 (Example 52) and differs from the present derivatives by having different substituents, in that the compounds hereof have an amide or substituted amide in place of the carboxylic acid group of the above patent.

SUMMARY OF THE INVENTION

The N-[[5-(trifluoromethyl)-6-methoxy-1-naphthalenyl]-thioxomethyl and carbonyl]-N-methylglycinamides of this invention are represented by formula I

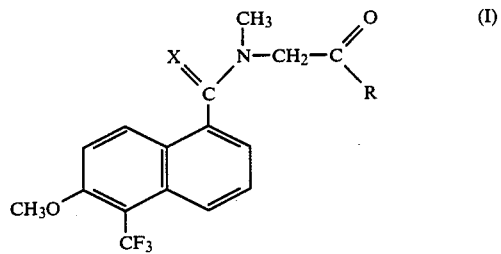

wherein R is selected from the group consisting of —NH$_2$, —NHCH$_3$, —N(CH$_3$)$_2$,

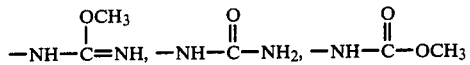

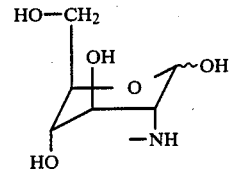

and X is oxygen or sulfur.

The N-[[5-(trifluoromethyl)-6-methoxy-1-naphthalenyl]-thioxomethyl and carbonyl]-N-methylglycinamides can be prepared by a process described hereinafter.

A method is provided for preventing or relieving diabetes mellitus associated complications in a diabetic mammal by administering to said mammal a prophylactic or alleviating amount of the compound of formula I. Such complications include neuropathy, nephropathy, retinopathy and cataracts.

The compound of formula I, when admixed with a pharmaceutically acceptable carrier, forms a pharmaceutical composition which can be used according to the preceding method.

DETAILED DESCRIPTION OF THE INVENTION

The compounds of this invention, represented by formula I, can exist in rotameric forms. More explicitly, mesomerism imparts a partial double bond character to the carbon-nitrogen bond of the thioamide group. This partial double bond character leads to restricted rotation about the carbon nitrogen bond giving rise to cis and trans rotamers, the restricted rotation being augmented by the bulkiness of neighboring groups. Interconversion of the rotameters is possible and is dependent on the physical environment. As evidenced by its physical properties, the thermodynamically more stable rotamer exists exclusively in the crystalline state of the compound and is the predominant isomer present in equilabrated solutions. Furthermore, the more stable rotamer is the more pharmacologically active. The less stable rotamer can be separated from the more stable rotamer by high performance liquid chromatography or by thin layer chromatography. The rotameric forms are included within the scope of this invention. For brevity, the compounds of this invention, including their rotameric forms, are referred to herein as compounds of formula I.

The N-[[5-(trifluoromethyl)-6-methoxy-1-naphthalenyl]-thioxomethyl and carbonyl]-N-methylglycinamides of this invention may be administered to mammals, for example, man, cattle or rabbits, either alone or in dosage forms, i.e., capsules or tablets, combined with pharmacologically acceptable excipients.

Advantageously the compounds of this invention may be given orally. However, the method of administering the present active ingredients of this invention is not to be construed as limited to a particular mode of administration. For example, the compounds may be administered topically directly to the eye in the form of drops of sterile, buffered ophthalmic solutions, preferably of pH 7.2–7.6. Also, they may be administered orally in solid form containing such excipients as starch, milk sugar, certain types of clay and so forth. They may also be administered orally in the form of solutions or they may be injected parenterally. For parenteral administration they may be used in the form of a sterile solution, preferably of pH 7.2–7.6, containing a pharmaceutically acceptable buffer.

The dosage of the N-[[5-(trifluoromethyl)-6-methoxy-1-naphthalenyl]-thioxomethyl and carbonyl]-N-methylglycinamides will vary with the form of administration and the particular compound chosen. Furthermore, it will vary with the particular host under treatment. Generally, treatment is initiated with small dosages substantially less than the optimal dose of the compound. Thereafter, the dosage is increased by small increments until efficacy is obtained. In general, the compounds of this invention are most desirably administered at a concentration level that will generally afford effective results without causing harmful or deleterious side effects. For topical administration, a 0.05–0.2% solution may be administered dropwise in the eye. The frequency of instillation varies with the subject under treatment from a drop every two or three days to once daily. For oral or parenteral administration a preferred level of dosage ranges from about 0.1 mg to about 200 mg per kilo of body weight per day, although aforementioned variations will occur. However, a dosage level that is in the range of from about 3.0 mg to about 30 mg per kilo of body weight per day is most satisfactory.

Unit dosage forms such as capsules, tablets, pills and the like may contain from about 5.0 mg to about 250 mg of the active ingredients of this invention with a pharmaceutical carrier. Thus, for oral administration, capsules can contain from between about 5.0 mg to about 250 mg of the active ingredients of this invention with or without a pharmaceutical diluent. Tablets, either effervescent or noneffervescent, can contain between about 5.0 to 250 mg of the active ingredients of this invention together with conventional pharmaceutical carriers. Thus, tablets, which may be coated and either effervescent or noneffervescent, may be prepared according to the known art. Inert diluents or carriers, for example, magnesium carbonate or lactose, can be used together with conventional disintegrating agents for example, magnesium stearate.

The N-[[5-(trifluoromethyl)-6-methoxy-1-naphthalenyl]-thioxomethyl and carbonyl]-N-methylglycinamides also can be used in combination with insulin or oral hypoglycemic agents to produce a beneficial effect in the treatment of diabetes mellitus. In this instance, commercially available insulin preparations or oral hypoglycemic agents, exemplified by acetohexamide, chlorpropamide, tolazamide, tolbutamide and phenformin, are suitable. The compounds hereof can be administered sequentially or simultaneously with insulin or the oral hypoglycemic agent. Suitable methods of administration, compositions and doses of the insulin preparation or oral hypoglycemic agent are described in medical textooks; for instance, "Physicians' Desk Reference", 36 ed., Medical Economics Co., Oradell, N.J. U.S.A., 1982. When used in combination, the N-[[5-(trifluoromethyl)-6-methoxy-1-naphthalenyl]-thioxomethyl and carbonyl]-N-methylglycinamides are administered as described previously. The N-[[5-(trifluoromethyl)-6-methoxy-1-naphthalenyl]-thioxomethyl and carbonyl]-N-methylglycinamides can be administered with the oral hypoglycemic agent in the form of a pharmaceutical composition comprising effective amounts of each agent.

The aldose reductase inhibiting property of the compounds of this invention and the utilization of the compounds in preventing, diminishing and alleviating diabetic complications are demonstrable in experiments using galactosemic rats, see Dvornik et al., cited above. Such experiments are exemplified hereinbelow after the listing of the following general comments pertaining to these experiments:

(a) Four or more groups of six male rats, 50–70 g, Sprague-Dawley strain, were used. The first group, the control group, was fed a mixture of laboratory chow (roden Laboratory Chow, Purina) and glucose at 20% (w/w %) concentration. The untreated galactosemic group was fed a similar diet in which galactose is substituted for glucose. The third group was fed a diet prepared by mixing a given amount of the test compound with the galactose containing diet. The concentration of galactose in the diet of the treated groups was the same as that for the untreated galactosemic group.

(b) After four days, the animals were killed by decapitation. The eyeballs were removed and punctured with a razor blade; the freed lenses were rolled gently on filter paper and weighed. The sciatic nerves were dissected as completely as possible and weighed. Both tissues when frozen can be kept up to two weeks before being analyzed for dulcitol.

(c) The polyol determination was performed by a modification of the procedure of M. Kraml and L. Cosyns, Clin. Biochem., 2, 373 (1969). Only two minor reagent changes were made: (a) The rinsing mixture was an aqueous 5% (w/v) trichloroacetic acid solution and (b) the stock solution was prepared by dissolving 25 mg of dulcitol in 100 ml of an aqueous trichloroacetic acid solution. [N.B.: For each experiment the average thioxomethyl and carbonyl]-N-methylglycinamides of this invention are surprisingly well suited as aldose reductose inhibitors. For example, compound No. 1 N-[[5-(trifluoromethyl)-6-methoxy-1-naphthalenyl]-thioxomethyl]-N-methylglycinamide at a dose of 5 mg/kg/day gives comparable results to compound No. 9 N-[[5-(trifluoromethyl)-6-methoxy-1-naphthalenyl]-thioxomethyl]-N-methylglycine. The latter compound, which is also known as tolrestat, (ALREDASE) is presently undergoing clinical trials.

| # | Test compound | % inhibition in vitro | mg/kg/day | % lowering dulcitol accumulation in vivo | | |
|---|---|---|---|---|---|---|
| | | | | L | N | D |
| | | $10^{-7}M$ | | | | |
| 1 | N—[[5-(trifluoromethyl)-6-methoxy-1-naphthalenyl]-thioxomethyl]-N—methylglycinamide | inactive | 5 | NS | 54 | 66 |
| 2 | 2-[[[6-methoxy-5-(trifluoromethyl)-1-naphthalenyl]thioxomethyl]methylamino]-N—methylacetamide | " | 50 | NS | 36 | 63 |
| 3 | 2-[[[6-methoxy-5-(trifluoromethyl)-1-naphthalenyl]thioxomethyl]methylamino]-N,N—dimethylacetamide | " | 55 | NS | 48 | 85 |
| 4 | N—[[[[5-(trifluoromethyl)-6-methoxy-1-naphthalenyl]thioxomethyl]-N—methylamino]acetyl]carbamimidic acid, methyl ester | " | 26 | 13 | 62 | 76 |
| 5 | [[[5-(trifluoromethyl)-6-methoxy-1-naphthalenyl]thioxomethyl](methylamino)-acetyl]urea | " | 23 | NS | NS | 64 |
| 6 | [[[5-(trifluoromethyl)-6-methoxy-1-naphthalenyl]thioxomethyl](methylamino)-acetyl]carbamic acid, methyl ester | " | 8.4 | NS | 33 | 69 |
| | | | 26 | NS | 93 | 88 |
| 7 | 2-deoxy-2-[[[[[6-methoxy-5-(trifluoromethyl)-1-naphthalenyl]-thioxomethyl]methylamino]acetyl]amino]-D-glucose | " | 161 | NS | NS | 37 |
| | | $(10^{-5}M)$ | | | | |
| 8 | N—[[6-methoxy-5-trifluoromethyl)-1-naphthalenyl]carbonyl]-N—methylglycinamide | inactive | 28 | — | 66 | 42 |
| 9 | N—[[5-(trifluoromethyl)-6-methoxy-1-naphthalenyl]-thioxomethyl]-N—methylglycine (tolrestat) | 79 | 4 | 0 | 35 | 80 |
| | | | 11 | 14 | 86 | 89 | value found in the tissue from rats fed the glucose diet was subtracted from the individual values found in the corresponding tissue in galactose-fed rats to obtain the amount of polyol accumulated.] The aldose reductase inhibiting effects of the compounds of formula (I) were also tested by employing an in vitro testing procedure similar to that described by S. Hayman and J. H. Kinoshita, J. Biol. Chem., 240, 877 (1965). In the present case the procedure of Hayman and Kinoshita was modified in that the final chromatography step was omitted in the preparation of the enzyme from bovine lens.

The following tabulated results show that the N-[[5]-(trifluoromethyl)-6-methoxy-1-naphthalenyl]-thioxomethyl and carbonyl]-N-methylglycinamides of this invention show the surprising property that they are inactive in vitro but in vivo diminish the accumulation of dulcitol in the lenses, sciatic nerves and diaphragm of rats fed galactose. The figures under L, N and D represent the percentage decrease of dulcitol accumulation in the tissues of the lens, sciatic nerve and diaphragm, respectively, for treated rats as compared to untreated rats.

Examination of the results tabulated below show that the N-[[5-(trifluoromethyl)-6-methoxy-1-naphthalenyl]-

THE PROCESS

The N-[[5-(trifluoromethyl)-6-methoxy-1-naphthalenyl]-thioxomethyl and carbonyl]-N- methylglycinamides can be prepared by the following reaction scheme:

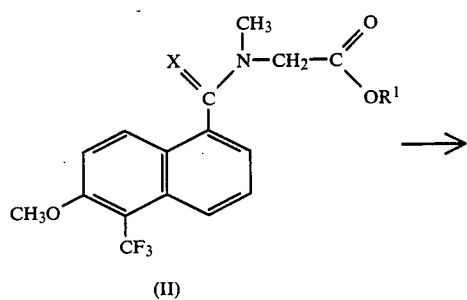

(II)

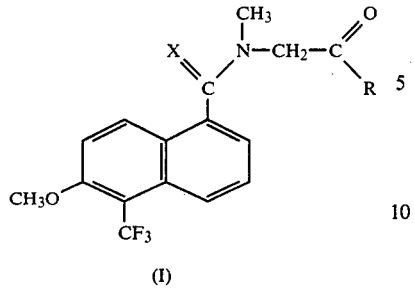

(I)

wherein N-[[5-(trifluoromethyl)-6-methoxy-1-naphthalenyl]-thioxomethyl and carbonyl]-N-methylglycine or an ester derivative thereof is reacted with ammonia or a suitably substituted amine to produce the amides of formula (I) wherein R is as defined above.

Specifically, tolrestat methyl ester (II, X=S, R¹=CH₃) treated with ammonia or monomethylamine gas in an alcohol solvent produces tolrestat amide (I, X=S, R=—NH₂) or the N-methyl amide (I, X=S, R=—NHCH₃).

Tolrestat activated with 1-(3-dimethylaminopropyl)-3-ethylcarbodiimide or dicyclohexylcarbodiimide in the presence of 1-hydroxybenzotriazole and subsequently treated with dimethylamine, glucosamine or O-methylisourea gives the corresponding tolrestat amides of structure (I, X=S) wherein R=—N(CH₃)₂,

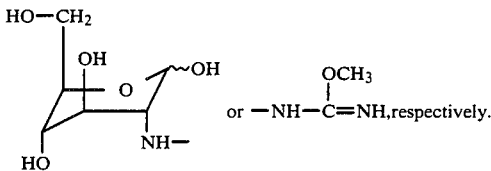

The compound of formula II, wherein X=S and R¹ is H is designated tolrestat. The compound of formula II, wherein X=O and R¹ is H is designated oxotolrestat.

The tolrestat amide derivative

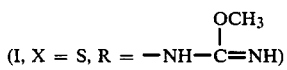

further treated with aqueous hydrochloric acid produces two products which are separated by chromatography on silica gel. The first product eluted with CHCl₃/MeOH is the carbamic acid, methyl ester derivative of tolrestat

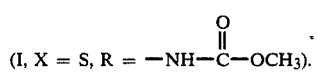

The second product eluted with the same solvent is the urea derivative of tolrestat

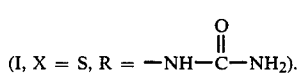

The following Examples further illustrate this invention.

EXAMPLE 1

N-[[5-Trifluoromethyl)-6-methoxy-1-naphthalenyl]-thioxomethyl]-N-methylglycinamide (I, X=S, R=—NH₂)

Dry ammonia gas was bubbled through a solution of the N-[[5-(trifluoromethyl)-6-methoxy-1-naphthalenyl]-thioxomethyl]-N-methylglycine, methyl ester (7 g, 0.0188 mol, prepared by the procedure of U.S. Pat. No. 4,439,617) in dry methanol (250 ml) to saturation. The mixture was warmed to 45° C. in a pressure bottle for 2 days with stirring. The solvent was evaporated and the product crystallized from methanol. Yield: 3 g., 45%, m.p. 168°–169° C. A further amount of 3 g of the crude material was obtained from the mother liquor (90% crude).

| Anal. Calcd: | C, 53.88% | H, 4.21% | N, 7.86% |
|---|---|---|---|
| Found: | 53.00 | 4.58 | 7.51 |

UV, $\lambda_{max}(\epsilon)$: 336(3700), 226(45,400).
MS: m/e 356 (M⁺), 339, 323, 269, 226, 207.

EXAMPLE 2

2-[[[6-Methoxy-5-(trifluoromethyl)-1-naphthalenyl]thioxomethyl]methylamino]-N-methylacetamide (I, X=S, R=—NHCH₃)

Dry monomethylamine gas was bubbled through a solution of the N-[[5-(trifluoromethyl)-6-methoxy-1-naphthalenyl]-thioxomethyl]-N-methylglycine, methyl ester (7 g, 0.0188 mol, prepared by the procedure of U.S. Pat. No. 4,439,617) in methanol (250 ml, dried over molecular sieves) at 0° C. for four hours. The solvent was evaporated and the product crystallized as a yellowish solid from aqueous methanol after charcoaling. Yield 6.60 g. (94.8%) m.p. 161°–163° C.

| Anal. Calcd: | C, 55.14% | H, 4.63% | N, 7.57% |
|---|---|---|---|
| Found: | 55.10 | 4.59 | 7.13 |

IR: (KBr, cm⁻¹): 3340 (—N—H); 1670 (—C=O); 1620 (—N—H).
UV: $\lambda_{max}(\epsilon)$: 337.5 (3879).
NMR (CDCl₃, δ): 2.57, 2.84(2d, 3H, HN—CH₃, rotamers); 3.00, 3.65(2s, 3H, N—CH₃, rotamers); 4.81 (2d, 2H, CH₂); 6.82(N—H); 7.33(m, 3H, aromatic); 8.16 (m, 2H, aromatic).
MS: (m/e) 370(M⁺), 269, 226, 101.

EXAMPLE 3

2-[[[6-Methoxy-5-(trifluoromethyl)-1-naphthalenyl]thioxomethyl]methylamino]-N,N-dimethylacetamide [I, X=S, R=—N(CH₃)₂]

N-[[5-Trifluoromethyl)-6-methoxy-1-naphthalenyl]-thioxomethyl]-N-methylglycine (3.6 g, 0.010 mol, prepared by the procedure of U.S. Pat. No. 4,439,617), 1-hydroxybenzotriazole (2 g, 0.015 mol), DMF (25 ml), (dried over molecular sieves) and 1-(3-dimethylaminopropyl)-3-ethylcarbodiimide hydrochloride (2.3 g, 0.012 mol), were combined with stirring, protected from moisture, and cooled in an ice bath. Triethylamine (3.5 ml, 0.025 mol) was added and stirring continued for two hours. Dry dimethylamine gas was bubbled through the cooled reaction mixture to saturation. The reaction mixture was stirred at room temperature over-night, evaporated in high vacuo, and the residue dissolved in water and ethyl acetate. The organic layer was washed with water, 2N, HCl, NaHCO$_3$ and water, dried over anhydrous magnesium sulfate and evaporated. The residue was dissolved in boiling ethyl ether (250 ml), ethyl acetate (50 ml), and hexane (100 ml) was added to crystallize. Yield 1.7 g, 42%, m.p. 172°–175° C. as a pale yellow powder.

| Anal. Calcd: | C. 56.19% | H, 4.94% | N, 7.28% |
|---|---|---|---|
| Found: | 56.11 | 4.98 | 7.21 |

IR: (CHCl$_3$, cm$^{-1}$); 1670 (C=O); 1625 (C=O, —N—H).

UV: $\lambda_{max}(\epsilon)$: 227.5 (45075).

NMR (CDCl$_3$, δ): 3.11 (d, 9H, N—CH$_3$); 4.01 (s, 3H, O—CH$_3$); 5.06 (2d, 2H, CH$_2$); 7.50 (m, 3H, aromatic); 8.37 (m, 2H, aromatic).

M.S. (m/e): 384(M+), 351, 269, 226, 207, 115, 72.

EXAMPLE 4

N-[[[5-(Trifluoromethyl)-6-methoxy-1-naphthalenyl]-thioxomethyl]methylamino]acetyl]carbamimidic Acid, Methyl Ester

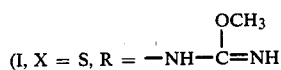

(I, X = S, R = —NH—C=NH

To a cooled and stirred solution of N-[[5-(trifluoromethyl)-6-methoxy-1-naphthalenyl]thioxomethyl]-N-methylglycine (3 g, 8.4 mmol) 1-hydroxybenzotriazole (1.7 g, 12.8 mmol), O-methylisourea bisulfate (1.6 g, 9.2 mmol) and triethylamine (1.86 g, 18.5 mmol, 2.6 ml) in dry dimethylformamide (15 ml) was added a solution of dicyclohexylcarbodiimide (2.1 g, 10 mmol) in dry dimethylformamide (15 ml). The mixture was allowed to attain room temperature, pH was adjusted to ~9 by addition of triethylamine. Additional amounts of DCCI (1 g) and O-methylisourea (0.3 g) were added and the mixture stirred over 24 hours at room temperature. Dicyclohexylurea was separated by filtration, the filtrate evaporated to dryness and the residue triturated with water and ethyl acetate. Separation of the phases was facilitated if some insoluble impurity was removed by filtration. The aqueous phase was repeatedly extracted with ethyl acetate, the organic layers washed with sodium bicarbonate solution, brine and dried over anhydrous MgSO$_4$. Evaporation to dryness and crystallization from toluene-hexane and recrystallization from toluene afforded 1.1 g (31.6% crude) of the product. Some dicyclohexylurea was removed by dissolving the crude material in ethyl acetate, filtration, evaporation and crystallization from toluene to give pure product (0.6 g, 17.2%) m.p. 165°–166° C. as a pale yellow powder.

| Anal. Calcd: | C, 52.30% | H, 4.39% | N, 10.16% |
|---|---|---|---|
| Found: | 52.21 | 4.48 | 10.22 |

IR (CHCl$_3$): 3480, 3300, 1630, 1600, 1500, 1330, 1100.
UV, $\lambda_{max}(\epsilon)$: 338 (3880), 227 (55,800).
NMR (CDCl$_3$): δ3.7 (2s, 3H, CH$_3$—N rotamers), δ3.9 (s, 3H, CH$_3$—O), δ4.0 (s, 3H, CH$_3$—O), δ5.0 (q, 2H, CH$_2$), δ7.3 (m, 3H, H$_{ar}$), δ8.3 (m, 2H, H$_{ar}$).

EXAMPLE 5

[[[5-(Trifluoromethyl)-6-methoxy-1-naphthalenyl]-thioxomethyl](methylamino)acetyl]urea

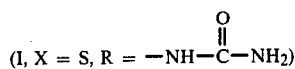

(I, X = S, R = —NH—C—NH$_2$)

The carbamimidic acid, methyl ester, prepared in Example 4, (4.5 g, 11 mmol,) was suspended in dioxane (90 ml) and 2N aqueous hydrochloric acid (22.5 ml) and the suspension was stirred at room temperature for 60 hours. After neutralization and evaporation to dryness the residue was triturated with water and extracted with ethyl acetate, the combined extracts dried and evaporated. The crude mixture of two products (5.5 g) 50% was purified by column chromatography (SiO$_2$, CHCl$_3$/MeOH 9:1). The product was eluted in the last fractions (2.2 g). It was purified by crystallization from toluene; yield 0.8 g. (18%) m.p. 203°–204° C. as a yellow powder.

| Anal. Calcd: | C, 51.12% | H, 4.04% | N, 10.52% |
|---|---|---|---|
| Found: | 51.54 | 4.09 | 10.33 |

IR (nujol): 3400, 3260, 3140, 1705, 1215, 1100 cm$^{-1}$.
UV, $\lambda_{max}(\epsilon)$: 337 (3890), 275 (12500), 227 (47400).
NMR (DMSO): δ3.02 (s, 3H, CH$_3$—N); δ4.05 (s, 3H, CH$_3$—O); δ4.75 and 5.43 (2d, 2H, N—CH$_2$CO, J=17); δ7.50 (br., 2H, NH$_2$); δ7.15–8.60 (m, 5H, H$_{ar}$); δ10.63 (s, 1H, NH).

MS: 399 (M+), 356, 339, 323, 311, 269, 266.

EXAMPLE 6

[[[5-(Trifluoromethyl)-6-methoxy-1-naphthalenyl]thioxomethyl](methylamino)acetyl]carbamic acid, Methyl Ester

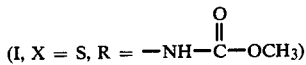

(I, X = S, R = —NH—C—OCH$_3$)

The first eluated fractions from chromatography (Example 5) were evaporated to dryness, and the crude carbamic acid, methyl ester (1.25 g, 27%) crytallized from toluene, giving 0.8 g, 17.5% of the pure product m.p. 178°–180° C. as pale yellow crystals.

| Anal. Calcd: | C, 52.17% | H, 4.14% | N, 6.76% |
|---|---|---|---|
| Found: | 52.18 | 4.17 | 6.70 |

IR (CHCl$_3$): 3380, 3240, 1760, 1715 cm$^{-1}$.
UV, $\lambda_{max}(\epsilon)$: 337 (3850), 272 (12,680), 227 (50,060), 211 (33,400).
NMR (CDCl$_3$): δ3.05 (s, 3H, N—CH$_3$); δ3.85 (s, 3H, OCH$_3$); δ4.0 (s, 3H, OCH$_3$); δ4.9 and 5.9 (2d, CH$_2$, J=17.5); δ7.4 (m, 4H, H$_{ar}$); δ7.8 (s, 1H, NH); δ8.3 (d, 1H, H$_{ar}$, J=9.5)

EXAMPLE 7

2-Deoxy-2-[[[[[6-methoxy-5-(trifluoromethyl)-1-naphthalenyl]thioxomethyl]methylamino]acetyl]amino]-D-glucose (I, X = S, R = 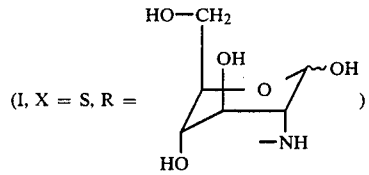 )

N-[[5-(Trifluoromethyl)-6-methoxy-1-naphthalenyl]-thioxomethyl]-N-methylglycine (3.57 g, 0.010 mol), 1-hydroxybenzotriazole (2 g, 0.015 mol), 1-(3-dimethylaminopropyl)-3-ethylcarbodiimide hydrochloride (2.3 g, 0.012 mol) and triethylamine (3.5 mol, 0.025 mol) were dissolved in dimethylformamide (25 ml). The mixture was cooled in ice and stirred for 1 hour. D-Glucosamine hydrochloride (2.38 g, 0.011 mol), and additional triethylamine (2.0 mol) were added to the cold reaction mixture. The reaction mixture was stirred at 0° C. for 1 hour, and at room temperature over night and evaporated. The residue was triturated with water and filtered. The solids were washed with $H_2O$, 1NHCl, 5% $NaHCO_3$, $H_2O$ and crystallized from 8/5 $H_2O$/MeOH to yield 3.63 g, 67.7%. The product was further purified by recrystallization from boiling methanol (3.1 g), m.p. 166°–169° C. (dec.) as yellow crystals.

| Anal. Calcd: | C, 49.24% | H, 5.07% | N, 5.22% |
|---|---|---|---|
| Found: | 49.39 | 5.23 | 5.13 |

IR (nujol, $cm^{-1}$): 3316 (N—H, OH); 1650 (C=O); 1620 (C=O, —N—H).

UV: $\lambda_{max}(\epsilon)$: 337.5 (3,763); 270.5 (11,767).

NMR (DMSO, δ): 3.00 (s, 3H, N—$CH_3$); 4.08 (s, 3H, O—$CH_3$); 6.62 (t, 1H, OH); 7.95 (m, 5H aromatic).

EXAMPLE 8

N-[[6-Methoxy-5-(trifluoromethyl)-1-naphthalenyl]carbonyl]-N-methylglycinamide (I, X=O, R=—$NH_2$)

The N-[[6-methoxy-5-(trifluoromethyl)-1-naphthalenyl]carbonyl]-N-methylglycine, methyl ester (3.6 g, 10.10 mmol) prepared according to U.S. Pat. No. 4,439,617, was stirred in a saturated solution of ammonia gas in methanol (40 ml) in a pressure vessel at 50° C. for 3 hours, then stirred for 16 hours at 20° C. The solvent was evaporated under reduced pressure. The residual oil was chromatographed on silica—9:1 ethyl acetate:methanol and the isolated product was recrystallized from ethyl acetate-petroleum ether to yield the pure product (2.8 g, 78%) m.p. 129°–131° C. as a white crystalline powder.

NMR (DMSO, δ): 2.75 (s, 3H, N—$CH_3$); 4.05 (s, 5H, —$OCH_3$, —$NCH_2$); 7.0–8.5 (m, 7H, ArH, $CON\underline{H}_2$)

IR (KBr, $cm^{-1}$) 3380, 3200 (—$CON\underline{H}_2$), 1670, 1640 (C=O), 1600, 1590 (C=C).

MS (Z/e) 340, 253.

UV $\lambda_{max}$ 233.5, 284, 296, 335.

| Anal. Calcd: | C, 56.47; | H, 4.44; | N, 8.23 |
|---|---|---|---|
| Found: | 56.57; | 4.45; | 8.03 |

We claim:
1. A compound of formula I

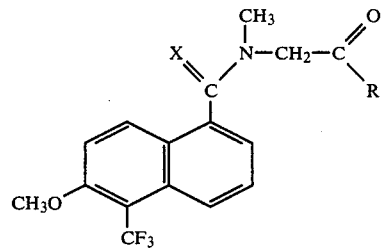

wherein R is selected from the group consisting of —$NH_2$, —$NHCH_3$, —$N(CH_3)_2$, $$-NH-\underset{\underset{OCH_3}{|}}{C}=NH, \quad -NH-\underset{\underset{O}{||}}{C}-NH_2, \quad -NH-\underset{\underset{O}{||}}{C}-OCH_3 \text{ and}$$

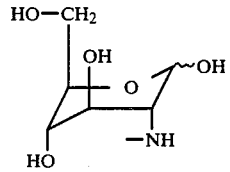

and X is oxygen and the pharmaceutically acceptable salts thereof.

2. The compound of claim 1 which is N-[[6-methoxy-5-trifluoromethyl)-1-naphthalenyl]carbonyl]-N-methylglycinamide.

3. A pharmaceutical composition for preventing or relieving neuropathy in a diabetic mammal, which comprises an effective amount of a compound of claim 1 and a pharmaceutically acceptable carrier.

4. A method of preventing or relieving neuropathy in a diabetic mammal, which comprises administering to said mammal an alleviating or prophylactic amount of a compound of claim 1.

5. A method of preventing or relieving nephtopathy in a diabetic mammal, which comprises administering to said mammal an alleviating or prophylactic amount of a compound of claim 1.

6. A method of preventing or relieving retinopathy in a diabetic mammal, which comprises administering to said mammal an alleviating or prophylactic amount of a compound of claim 1.

7. A method of preventing or relieving cataracts in a diabetic mammal, which comprises administering to said mammal an alleviating or prophylactic amount of a compound of claim 1.

* * * * *